US009717837B2

(12) United States Patent
Vincent (10) Patent No.: US 9,717,837 B2
(45) Date of Patent: Aug. 1, 2017

(54) DIALYSIS MACHINE INCLUDING ULTRAFILTRATION AND BACKFILTRATION MEANS

(71) Applicant: PHYSIDIA, Saint-Barthelemy-d'Anjou (FR)

(72) Inventor: Eric Vincent, Angers (FR)

(73) Assignee: PHYSIDIA, Saint-Barthelemy-d'Anjou (FR)

( * ) Notice: Subject to any disclaimer, the term of this patent is extended or adjusted under 35 U.S.C. 154(b) by 492 days.

(21) Appl. No.: 14/349,078

(22) PCT Filed: Sep. 28, 2012

(86) PCT No.: PCT/FR2012/052198
§ 371 (c)(1),
(2) Date: Apr. 2, 2014

(87) PCT Pub. No.: WO2013/050689
PCT Pub. Date: Apr. 11, 2013

(65) Prior Publication Data
US 2014/0238912 A1    Aug. 28, 2014

(30) Foreign Application Priority Data
Oct. 3, 2011    (FR) ..................................... 11 58915

(51) Int. Cl.
*A61M 1/16*    (2006.01)
*A61M 1/34*    (2006.01)
(Continued)

(52) U.S. Cl.
CPC ............ *A61M 1/34* (2013.01); *A61M 1/1635* (2014.02); *A61M 1/342* (2013.01);
(Continued)

(58) Field of Classification Search
CPC ...... A61M 1/34; A61M 1/342; A61M 1/3424; A61M 1/3427; A61M 1/3437;
(Continued)

(56) References Cited

U.S. PATENT DOCUMENTS 4,762,618 A    8/1988    Gummesson
5,011,607 A    4/1991    Shinzato
(Continued)

FOREIGN PATENT DOCUMENTS

CN    1309572    8/2001
CN    1188179 C    2/2005
(Continued)

OTHER PUBLICATIONS

International Search Report dated Dec. 3, 2012, corresponding to PCT/FR2012/052198.
(Continued)

*Primary Examiner* — Joseph Drodge
(74) *Attorney, Agent, or Firm* — Ipsilon USA, LLP (57) ABSTRACT

A dialysis machine includes a dialyzer (1), a dialysate feed system (5) having a feed line (52), and a discharge system (6) having a discharge line (62). The machine further includes ultrafiltration control elements (UF) and back-filtration control elements (RF). The feed line is provided with a constriction (520) and with elements for measuring the pressure difference (523, 524) across the terminals of the constriction. The feed system further includes a ventricle bag (50), and pressurizer elements (70) for putting the ventricle bag (50) under pressure. The machine further includes an open/close system (C5, C5') for opening/closing the discharge line (62) and the back-filtration control elements cause the discharge line (62) to close, and control the pressure applied to the ventricle bag (50), as a function of the pressure difference measured across the terminals of the
(Continued)

constriction (520), so as to obtain a given flow rate of dialysate.

20 Claims, 6 Drawing Sheets

(51) Int. Cl.
  *B01D 61/28* (2006.01)
  *B01D 61/30* (2006.01)
  *B01D 61/32* (2006.01)
(52) U.S. Cl.
  CPC ........ *A61M 1/3427* (2014.02); *A61M 1/3465* (2014.02); *B01D 61/28* (2013.01); *B01D 61/32* (2013.01)
(58) Field of Classification Search
  CPC .... A61M 1/3462; A61M 1/3465; A61M 1/16; A61M 1/1601; A61M 1/1603; A61M 1/1635; A61M 1/1647; A61M 1/1656; B01D 61/24; B01D 61/243; B01D 61/30; B01D 61/32; B01D 61/34; B01D 61/28
  USPC ............. 210/90, 97, 137, 257.2, 258, 321.6, 210/321.71, 416.1, 637, 646, 647, 741; 604/4.01–6.11, 29–31, 65–67
  See application file for complete search history.

(56) References Cited

U.S. PATENT DOCUMENTS

| | | | |
|---|---|---|---|
| 5,700,372 A * | 12/1997 | Takesawa | A61M 1/342 210/321.6 |
| 6,011,067 A | 1/2000 | Hersh | |
| 2001/0035378 A1 | 11/2001 | Nikaido et al. | |
| 2002/0023879 A1 | 2/2002 | Hadden | |
| 2003/0220598 A1 | 11/2003 | Busby et al. | |
| 2006/0138049 A1 * | 6/2006 | Kim | A61M 1/30 210/646 |
| 2009/0008306 A1 | 1/2009 | Cicchello et al. | |
| 2013/0199998 A1 * | 8/2013 | Kelly | A61M 1/1696 210/646 |
| 2013/0213890 A1 * | 8/2013 | Kelly | A61M 1/16 210/646 |
| 2013/0256227 A1 * | 10/2013 | Kelly | A61M 1/3621 210/638 |

FOREIGN PATENT DOCUMENTS

| | | | |
|---|---|---|---|
| EP | 0 204 174 | | 12/1986 |
| EP | 1779880 | * | 5/2007 |
| JP | 60158864 | | 8/1985 |
| JP | 2006238915 | | 9/2006 |
| JP | 2007510473 | | 4/2007 |
| WO | 2004009158 | | 1/2004 |
| WO | 2007143497 | | 12/2007 |

OTHER PUBLICATIONS

Search Report Dated Sep. 28, 2012.
Office Action Dated May 10, 2016.
CN Search Report Dated May 10, 2016.

* cited by examiner

DIALYSIS MACHINE INCLUDING ULTRAFILTRATION AND BACKFILTRATION MEANS

The present invention relates generally to dialysis machines, in particular for hemodialysis.

The invention relates more particularly to a dialysis machine making it possible to treat a body fluid or "corporeal liquid", such as blood or plasma. Said machine includes a dialyzer having an enclosure housing a dialysis membrane that subdivides the enclosure into a body fluid compartment, and a dialysate compartment. Said body fluid compartment has a body fluid inlet and a body fluid outlet, and said dialysate compartment has a dialysate inlet and a dialysate outlet. Said machine also includes a dialysate feed system that comprises a dialysate feed line connected to the inlet of the dialysate compartment, and a dialysate discharge system that comprises a dialysate discharge line connected to the outlet of the dialysate compartment. Said machine also includes a control unit, such as a programmable controller, which comprises ultrafiltration control means (UF) making it possible to cause an aqueous quantity of body fluid to pass through at least a portion of the membrane from the body fluid compartment into the dialysate compartment, and back-filtration or "retrofiltration" control means making it possible to cause the dialysate to pass through at least a portion of the membrane from the dialysate compartment into the body fluid compartment.

In general, hemodialysis consists in purifying the blood of substances present in excess such as urea, vitamin B12, beta-immunoglobulin, or indeed mineral salts. Such excess substances can be removed by osmosis by causing the blood to flow along one side of the membrane, and by causing the dialysate to flow along the other side of the membrane. Thus, the substances present in excess in the blood diffuse through the membrane into the dialysate.

It is also possible to extract an aqueous fraction from the blood in an "ultrafiltration" operation. Ultrafiltration results from a convection phenomenon through the membrane. Under the effect of pressure in the blood compartment that is greater than the pressure in the dialysate compartment, an aqueous fraction of the blood is pushed through the membrane, thereby reducing the volume of blood. Blood is made up of water, of mineral salts, and of numerous substances and cells, such as red corpuscles. Said aqueous fraction of the blood that this convection mechanism causes to pass through the membrane, comprises, in particular, water, mineral salts, and molecules of small or medium molecular weight, such as vitamin B12.

Conversely to an ultrafiltration operation, it is also possible to cause a suitable quantity of dialysate to pass into the blood in a "back-filtration" or "retrofiltration" operation. Generally, the dialysate then serves both as an exchange liquid for exchanging with the blood and as a substitute liquid introduced directly into the bloodstream of the patient.

A dialysis machine as described above is known from the state of the art, and in particular from Document U.S. Pat. No. 5,011,607. However, in Document U.S. Pat. No. 5,011,607, the back-filtration control means are complex and lack accuracy because they require the presence of at least one pump upstream from the dialysate compartment and of at least one pump downstream from the dialysate compartment. Since the pressure in the dialysate compartment is a function of the difference between the flow rates imposed by the upstream and downstream pumps, it is necessary to control the flow rates of those two pumps accurately, which complicates controlling the machine and increases the risk of errors. And yet the flow rate of back-filtered dialysate needs to be regulated very accurately so as not to endanger the life of the patient.

Since it is necessary to control an upstream pump and a downstream pump in the dialysate circuit in order to back-filter a given quantity of dialysate, it is necessary to regulate the flow rate of each of the pumps and, to that end, to measure the corresponding upstream and downstream flow rates in the dialysate circuit. As a result, the flow rate measurement error associated with the upstream pump is additional to the flow rate measurement error associated with the downstream pump. Furthermore, the flow-rate control errors associated with the two pumps are also cumulative.

Finally, the pumps that are usually used to cause dialysate to flow are pumps of the peristaltic type that have low operating accuracy. A peristaltic pump uses rollers that squeeze a pipe to cause the dialysate to flow. Not only is the flow-rate control that is obtained with such rollers inaccurate, but also the pipe deteriorates rapidly so that the dialysate flow rate cannot be determined accurately and reliably. Thus, such a pump does not make it possible to cause a given flow rate of dialysate to be obtained with sufficient accuracy for a back-filtration operation in which it must be possible for the flow rate of back-filtered dialysate to be determined accurately and reliably so as not to endanger the life of the patient.

It is also known that constant-volume pumps can be used to cause the dialysate to flow. However, each time the pump is activated, such a pump causes a predefined given volume of dialysate to flow, which does not make it possible to obtain a flow-rate of dialysate that is sufficiently accurate and regular at the inlet of the dialysate compartment during an ultrafiltration step and/or during a back-filtration step.

In addition, with such machines known from the state of the art, it is necessary to perform operations of cleaning, sterilizing, and rinsing all of the components of the dialysate circuit that have been in contact with the dialysate, such as the pipes of the pumps and the flow meters. When more than one patient is treated, then between each dialysis session, the dialyzer filter is changed, and the blood access lines connecting the patient to the dialyzer on the arterial and venous sides are discarded, and the piping of the machine is cleaned, chemically or thermally sterilized, and rinsed, in particular the upstream and downstream dialysate lines and the members through which the dialysate passes, such as the pumps and valves.

Those operations are lengthy, and costly, and the risks of contamination remain high.

Finally, it is desirable to be able to improve the treatment proposed in Document U.S. Pat. No. 5,011,607. Control of the back-filtration and ultrafiltration operations proposed in that document is limited to removing a given volume of aqueous fraction of the patient's blood by ultrafiltration and to replacing that volume with the same volume of dialysate.

An object of the present invention is to propose a novel dialysis machine enabling the ultrafiltration and back-filtration operations to be controlled accurately and reliably. In particular, an object of the invention is to enable the flow rate of dialysate entering the dialysate compartment to be controlled accurately and reliably.

Another object of the present invention is to propose a novel dialysis machine that is simplified, that is of low cost, and with which the risk of contamination of the body fluid to be treated is very low.

To this end, the invention provides a dialysis machine making it possible to treat a body fluid, such as blood or plasma, said machine comprising:

a dialyzer including an enclosure housing a dialysis membrane that subdivides the enclosure into a compartment for passing said body fluid and referred to as the "body fluid compartment", and a compartment for passing dialysate and referred to as a "dialysate compartment";

said body fluid compartment having a body fluid inlet and a body fluid outlet, and said dialysate compartment having a dialysate inlet and a dialysate outlet;

a dialysate feed system comprising a dialysate feed line connected to the inlet of the dialysate compartment; and a dialysate discharge system comprising a dialysate discharge line connected to the outlet of the dialysate compartment;

a control unit, such as a programmable controller, that comprises:

ultrafiltration control means making it possible to cause an aqueous quantity of the body fluid to pass through a portion of the membrane from the body fluid compartment into the dialysate compartment; and back-filtration control means making it possible to cause the dialysate to pass through at least a portion of the membrane, from the dialysate compartment into the body fluid compartment;

said dialysis machine being characterized in that the dialysate feed line is provided with a flow constriction, and said machine further comprises means for measuring the pressure difference across the terminals of said flow constriction;

in that said dialysate feed system further comprises:

at least one flexible bag, referred to as a "ventricle bag", designed to contain the dialysate and connected to said feed line upstream from said flow constriction, said ventricle bag being contained in an enclosure; and pressurizer means for putting the ventricle bag under pressure by pressurizing said enclosure;

and in that said machine further comprises an open/close system for opening/closing the dialysate discharge line, which system, when in the open state, allows the dialysate present at the outlet of the dialysate compartment to flow through said discharge line, and, when in the closed state, prevents the dialysate present at the outlet of said dialysate compartment from flowing through said discharge line;

said back-filtration control means being configured to:

control said open/close system so as to close the discharge line; and when said discharge line is in the closed state, control the pressure applied to said ventricle bag as a function of the pressure difference measured across the terminals of the constriction, so as to obtain a given flow rate of dialysate.

Closing the discharge line by means of said open/close system in order to cause a back-filtration operation to take place makes it simple to control the pressurizer means for putting the ventricle bag under pressure in order to obtain the desired flow rate of dialysate for a given time in order to back-filter the desired quantity of dialysate.

Since the discharge line is closed, the dialysate, fed into the dialysate compartment by applying pressure to the ventricle bag, can exit from the dialysate compartment only through the membrane into the body fluid compartment. As a result, the flow rate of dialysate that flows through the feed line corresponds to the flow rate of back-filtered dialysate.

Thus, contrary to the solutions known from the state of the art, it is not necessary, during the back-filtering operation, to control a pump situated downstream from the outlet of the dialysate compartment in order to adjust the upstream and downstream flow rates of dialysate. With the invention, the downstream flow rate is zero because the discharge line is closed and the flow-rate of back-filtered dialysate corresponds to the flow rate of dialysate entering the dialysate compartment.

Controlling the back-filtration operation is thus simplified and can take place with great accuracy since not only does the flow meter, formed by the flow constriction and the means for measuring pressure difference, make it possible to obtain a given flow rate with great accuracy, but also, the back-filtered flow rate does not depend on any flow rate downstream in the discharge line, which makes it possible to be exempt from the accuracy errors of any downstream pump such as used in machines known from the state of the art.

It should be noted that, as explained above, using a peristaltic pump instead of the pressurizer means and of the flexible bag would not make it possible to impose a given flow rate of dialysate in a stable and sufficiently accurate manner. With the machine of the invention, implementing the dialysate pump in the form of a flexible ventricle bag, housed in an enclosure and associated with pressurizer means for pressurizing the enclosure, makes it possible to apply pressure to the bag in reliable and accurate manner and thus, in co-operation with the flow meter formed of the flow constriction and of the corresponding pressure sensors, to obtain a flow rate of fluid that is more accurate than the flow rate of fluid that can be obtained with a peristaltic pump that uses rollers for flattening a tube. Similarly, as explained above, using a constant-volume pump would not be accurate enough to obtain the desired flow rate of dialysate.

Controlling the pressure applied to the ventricle bag as a function of the pressure difference measured across the terminals of the constriction makes it possible to regulate said pressure applied to the bag so as to maintain a given flow rate for a given time so as to obtain a quantity of back-filtered dialysate in an accurate and reliable manner.

In particular, controlling the pressure applied to the bag and regulating it by means of the flow meter, formed by the constriction and the associated means for measuring pressure difference, makes it possible to maintain the mean pressure in the dialysate compartment at a given value. That value is determined by the control unit so that, in view of the mean pressure in the blood compartment and of the characteristics of the membrane, a given flow rate of dialysate is back-filtered for a given duration. Measuring the pressure difference across the terminals of the constriction enables the control unit, and in particular the back-filtration control means, to regulate the control of the pressure applied to the ventricle bag so as to maintain the pressure in the dialysate compartment and thus the flow rate of back-filtered dialysate at a given value for said back-filtration duration.

When the open/close system of the discharge line is in the open position, the dialysate can flow out from the ventricle bag through the feed line, through the dialysate compartment, and through the discharge line. When the ultrafiltration control means cause the discharge line to open, the mean pressure in the dialysate compartment, which pressure is generated by the dialysate that flows out from the ventricle bag, is maintained less than the mean pressure in the body fluid compartment so that an aqueous fraction of the body fluid passes from the body fluid compartment to the dialysate compartment, entraining water and certain uremic toxins.

In addition, the design of the dialysate feed system in the form of at least one ventricle bag and of pressurizer means, and the presence of a flow constriction in the feed line so as to co-operate, in combination with means for measuring pressure difference, to form a flow meter, makes it possible to design the dialysate circuit in the form of a disposable circuit in which the components that come into contact with the dialysate are simple and low-cost, thereby making it possible to replace them for each session and thus to ensure that the machine continues to be sterile from one session to another. As described in detail below, the other components, such as the means for measuring pressure difference and the open/close system for opening/closing the discharge line, are arranged in such a manner as not to come into contact with the dialysate.

In particular, the dialysate lines and bags can be discarded after the session, which obviates the need to sterilize and to rinse the machine. It is not necessary to sterilize the pressurizer means because they apply a gas pressure to the wall of the bag or of each bag and do not come into direct contact with the liquid. The ventricle bag is easy to discard and to replace by opening the enclosure in which it is housed. The dialyzer, the dialysate and blood lines, the bags, and the head-loss tubes are inexpensive and can thus be single-use components.

In accordance with an advantageous characteristic of the invention, said dialysate discharge system further comprises at least one discharge bag that is preferably flexible and that has an inlet and an outlet that are connected to the dialysate discharge line;

and said open/close system comprises an upstream open/close member situated between the outlet of the dialysate compartment and said discharge bag;

and said machine further comprises means for determining the quantity of dialysate and of liquid recovered in said discharge bag.

Said discharge bag makes it possible, when the discharge line is in the open configuration, to recover the dialysate that has flowed from the ventricle bag and the aqueous fraction extracted from the body fluid by ultrafiltration, in such a manner as to determine the aqueous quantity extracted from the body fluid. It suffices to subtract from the total quantity recovered in the discharge bag the quantity of dialysate that has flowed from the ventricle bag in order to determine said aqueous quantity extracted from the body fluid. Knowledge of that aqueous quantity makes it possible to compute the quantity of liquid to be back-filtered and optionally to adjust the aqueous quantity to be extracted and/or to be back-filtered during the next cycle.

Preferably, said dialysate discharge system further comprises at least one other discharge bag connected in parallel with said discharge bag;

and said open/close system further comprises another upstream open/close member situated between said other discharge bag and the connection inlet node for connection to the discharge bags;

and said machine further comprises means for determining the quantity of dialysate and of liquid recovered in said other discharge bag.

The presence of two discharge bags connected in parallel makes it possible to limit the dead time for which the machine cannot operate, because it is thus possible to empty one of the previously filled discharge bags while the other discharge bag is filling.

Advantageously, said means for determining the quantity of dialysate and of liquid recovered in the discharge bag(s) comprise a flow constriction provided in the dialysate discharge line and situated downstream from said discharge bag(s), and measurement means for measuring the pressure difference across the terminals of said flow constriction.

Such means for measuring the pressure difference across the terminals of said flow constriction of the discharge line make it possible to determine the flow-rate discharged from said discharge bag or from one of said discharge bags, and thus to determine, by measuring the corresponding flow time, the quantity of dialysate and of liquid recovered in said discharge bag.

The or each ventricle bag and the or each discharge bag are distinct from each other so that, when the upstream open/close member, associated with the discharge bag or with one of the discharge bags, is in the closed position, the ventricle bag or one of the ventricle bags can be pressurized without that having any influence on said discharge bag. In other words, said bags do not share any common wall or have any walls in direct contact. Such a design for the bags makes it possible to empty the or each discharge bag during an ultrafiltration step or during a back-filtering step, and therefore without dedicating extra time to such emptying.

In accordance with an advantageous characteristic of the invention, said means for measuring the pressure difference across the terminals of the constriction in the feed line, or, respectively across the terminals of the constriction in the discharge line when said constriction is present, comprise:

two orifices, referred to as "pressure measurement orifices", one of which is provided upstream from said constriction and the other which is provided downstream from said constriction; and for each pressure measurement orifice, a pressure sensor arranged in such a manner as to measure the pressure in the corresponding line at said orifice while also being spaced apart from said orifice so as not to be in contact with the dialysate flowing through the line.

It is thus possible to discard the dialysate lines while also preserving the sensors because they are protected from the dialysate. As a result, the cost of using the machine is low while preserving a very low risk of contamination.

Preferably, a filter that is permeable to air and impermeable to infectious agents and to liquids is interposed between each pressure sensor and the corresponding pressure measurement orifice.

In the event that drops of dialysate flow through the corresponding pressure measurement orifice, said filter makes it possible to intercept the drops and thus to preserve the sensor from any risk of contamination.

Advantageously, said machine has a frame, and said pressure sensors are fastened to the frame of the machine, and the dialysate feed line and the dialysate discharge line are suitable for being removed from the remainder of the machine, while the corresponding pressure sensors remain fastened to the frame of the machine.

As described above, between each dialysis session, the dialyzer and the blood access lines on the arterial and venous sides are discarded and replaced. The ventricle and discharge bags, and the feed and discharge lines are also discarded and replaced. But the pressure sensors remain in place in the machine. During the preceding treatment session, said pressure sensors remained protected from the dialysate by means of them being spaced apart from the pressure measurement orifice and, preferably, by means of the filter incorporated in a duct interposed between the sensor and the pressure measurement orifice. Thus, with the machine of the invention, it is thus no longer necessary to sterilize the piping of the machine chemically or thermally, or to rinse the piping of the machine. The components of the machine that have been in contact with the dialysate are low cost and are separable from the frame of the machine, enabling them to be discarded and replaced easily.

In addition, incorporating the pressure sensors in the frame of the machine makes it possible to design a machine that is compact.

In accordance with an advantageous characteristic of the invention, in order to cause the dialysate discharge line to be closed with a view to performing a back-filtration step, said back-filtration control means are configured to cause each of said upstream open/close members associated with the discharge bags to close;

and, in order to cause the dialysate discharge line to be opened with a view to performing an ultrafiltration step, said ultrafiltration control means are configured to cause one of said upstream open/close members to open, and to cause the other upstream open/close member to close;

said ultrafiltration control means preferably being configured to act, in the next ultrafiltration step, to cause the other of said upstream open/close members to open and to cause said upstream open/close member to close.

Thus, the discharge bags are filled in alternation, thereby making it possible to empty one of them while the other is filling.

Advantageously, the or each discharge bag is provided with a "downstream" open/close member situated downstream from said discharge bag;

and, after an ultrafiltration step, said control unit is configured to act, preferably in parallel with a back-filtration step, to cause the downstream open/close member of the previously filled discharge bag to open in order to discharge its contents;

and, preferably, in order to determine the quantity recovered in said discharge bag, the control unit is configured to measure the flow rate that flows from said discharge bag, using said means for measuring the pressure difference across the terminals of the constriction situated downstream from said discharge bag.

Said constriction in the discharge line is also situated downstream from the open/close member associated with the or each discharge bag.

Measuring the quantity of dialysate and of liquid recovered in the discharge bag can thus be achieved reliably and without requiring dedicated time, in parallel with an ultrafiltration step and/or with a back-filtration step.

In accordance with an advantageous characteristic of the invention, said control unit further comprises means for determining an excess aqueous quantity to be removed from the body fluid, which quantity is referred to as the "excess aqueous quantity";

and the ultrafiltration control means are configured to extract through the dialysis membrane an aqueous quantity of the body fluid, which quantity is referred to as the "gross aqueous quantity to be removed" and is greater than said excess aqueous quantity that is defined;

the back-filtration control means being configured to back-filter a quantity of dialysate that is substantially equal to the difference between said gross aqueous quantity to be removed and said excess aqueous quantity.

By removing from the body fluid an aqueous quantity that is greater than the excess quantity and by compensating for the removed extra amount by injecting dialysate into said body fluid, it is possible to purify said body fluid in quick and effective manner.

Advantageously, said control unit is configured to act during a treatment session to cause ultrafiltration steps to take place in alternation with back-filtration steps, the number of alternations preferably being not less than 1000.

Such an alternation of back-filtration and ultrafiltration steps makes it possible to treat the body fluid rapidly and homogeneously so that said body fluid treated in this way can be re-injected into the body of the patient without any risk of unbalancing the patient's physiological parameters. Such alternation also makes it possible to optimize the effectiveness of the membrane by reducing the risk of the membrane clogging and the risk of coagulation when said body fluid is blood.

In accordance with an advantageous characteristic of the invention, for a number, referenced N, of cycles, each cycle $i$, where $i$ lies in the range 1 to N, is made up of an ultrafiltration step of duration $Te\_uf\_i$ and of a back-filtration step of duration $Te\_rf\_i$;

said control unit is configured to:
determine the excess aqueous quantity in the body fluid, referenced $Q\_aq\_excess$ that is to be removed;
for each cycle $i$, define the durations $Te\_uf\_i$ and $Te\_rf\_i$, and control the pressurizer means in such a manner that:
$Q\_aq\_excess$=Sum over i, where i lies in the range 1 to N, of $$K \times [(Pa\_i + Pv\_i)/2 - P14\_uf\_i] \times Te\_uf\_i - (Dd\_rf\_i \times Te\_rf\_i)$$

where:
K is a predefined coefficient of ultrafiltration that is specific to the membrane and that expresses the ultrafiltration capacity thereof;
$Pa\_i$ is the pressure upstream from the body fluid compartment during the ultrafiltration step of the cycle $i$;
$Pv\_i$ is the pressure downstream from the body fluid compartment during the ultrafiltration step of the cycle $i$;
$P14\_uf\_i$ is the mean pressure in the dialysate compartment during the ultrafiltration step of the cycle $i$; and
$Dd\_rf\_i$ is the flow rate of dialysate in the dialysate compartment during the back-filtration step of the cycle $i$.

It is thus possible to control the aqueous quantity that is extracted from the body fluid and the quantity of dialysate that is reinjected by adjusting the durations $Te\_uf\_i$ and $Te\_rf\_i$ and to control the pressure applied to the corresponding ventricle bag.

In accordance with an advantageous characteristic of the invention, said open/close system for opening/closing the discharge line comprises at least one clamp suitable firstly for clamping, from the outside, the wall of a flexible portion of said discharge line in such a manner as to close said portion, and secondly for leaving said flexible portion of said discharge line open.

Opening/closing said discharge line using a clamp making it possible firstly to clamp a flexible portion of the line so as to prevent flow through said portion, and, secondly to leave the portion unobstructed so as to allow said flow, makes it possible for the corresponding portion of the discharge line to be closed rapidly and reliably. In addition, the use of such a clamp external to the discharge line makes it possible to cause the corresponding portion of the discharge line to close/open without any risk of contaminating the clamp because said clamp is not in contact with the liquid present in the discharge line. Thus, such a clamp can be reused without having to be cleaned, unlike when an on/off valve or a proportional valve is used, in contact with the dialysate.

In accordance with an advantageous characteristic of the invention, each of the upstream close/open members, and, optionally, each of the downstream close/open members, for closing/opening the discharge line comprises at least one clamp suitable firstly for clamping, from the outside, the wall of a flexible portion of said discharge line in such a manner as to close said portion, and secondly for leaving said flexible portion of said discharge line open.

Thus, the close/open system for closing the discharge line may be implemented in simple and inexpensive manner. As explained above, each clamp is isolated from the liquid present in the discharge line and thus does not need to be cleaned or discarded.

In accordance with an advantageous characteristic of the invention, the dialysate feed system further comprises an additional ventricle bag, the two ventricle bags being suitable for being put under pressure separately by said pressurizer means. Each ventricle bag is housed in a substantially sealed enclosure suitable for being put under pressure by said pneumatic means for putting said ventricle bag under pressure.

Said dialysis machine advantageously includes means for opening and for closing, in alternation, the connection ducts connecting the ventricle bags to the feed line. Said means for opening and closing the connection ducts in alternation are preferably formed by a system of clamping said ducts in alternation.

Such use of two ventricle bags connected in parallel makes it possible to avoid any interruption in the flow rate of dialysate and to avoid dead times for which the machine cannot operate. The ventricle bags are used in alternation so that one of the ventricle bags can be being filled while the other ventricle bag is delivering the dialysate.

In addition, the design of the upstream and downstream dialysate flow system in the form of ventricle bags and of substantially sealed enclosures, makes it possible, between two sessions to replace the ventricle bags of the dialysate circuit easily and quickly with other sterile bags, merely by opening the enclosure, in order to limit the risk of contamination.

In accordance with an advantageous characteristic of the invention, said or each ventricle bag is also provided with an inlet for connection to a dialysate feed source, preferably a feeder bag that is of larger volume than the or each ventricle bag.

For "frequent or daily" dialysis treatment, made up of shorter sessions but over a larger number of days in comparison to conventional dialyses that take place in hospital, the volumes of dialysate necessary for each session are smaller so that the use of ready-to-use feeder bags containing dialysate is particularly appropriate. Such frequent or daily dialysis offers the therapeutic advantage of minimizing the amplitudes of the physiological parameters, such as toxin concentrations or levels of overweight.

Treating a patient at relatively long intervals constitutes a major drawback. The patient then, between the sessions, stores large amounts of toxins and of excess water, and treating the patient then requires sessions that are lengthy and tiring for the patient and equipment that is complex, in particular because of the large quantities of ultrapure dialysate to be prepared.

Daily dialysis can thus be performed with less dialysate per session, thereby making it possible to use bags and thus to avoid the need to have a machine that generates dialysate continuously. Daily dialysis can thus be performed at home, thereby making it possible to save the cost of transporting the person requiring dialysis. Since the dialysate is ready to use in bags, the workload and supervision/monitoring related to preparing dialysate is reduced.

The invention can be well understood on reading the following description of embodiments given with reference to the accompanying drawings, in which.

With reference to the figures, and as stated above, the invention relates to a dialysis machine making it possible to treat a body fluid or "corporeal liquid", such as blood or plasma. The term "body fluid" is used to mean a liquid of the types present in the human or animal body, such as blood or plasma.

It should be noted that the dialysis machine of the invention is described below in the context of when the body fluid to be purified is blood. Blood is made up of water, of mineral salts, and of numerous substances and cells, such as red corpuscles. Naturally, the description of the machine below also applies to a body fluid other than blood.

Said machine includes a dialyzer 1 having an enclosure housing a dialysis membrane 3 that subdivides the enclosure into a blood compartment 12 and a dialysate compartment 14.

Dialysate is a liquid that is well known to the person skilled in the art and its composition is close to physiological serum. Dialysate includes water that is of sufficient mineralogical and bacteriological quality. This purified water is added to a concentrate, in the form of mineral salt powder or in the form of liquid concentrate, for preparing the required dialysate.

The dialysate flows through the dialysate compartment 14, generally in the direction opposite from the direction in which the blood flows through the other compartment 12. The dialysate generally flows in an open circuit. It is also possible to provide a regeneration loop for partially regenerating clean dialysate from the dialysate loaded with toxins.

The semi-permeable dialysis membrane 3 is designed in such a manner as to allow a fraction of the blood volume to pass through when the difference between the local pressure in the blood compartment 12 and the local pressure in the dialysate compartment 14 is greater than a given value. This pressure difference is referred to as the "transmembrane pressure". In particular, the membrane is designed in such a manner that only the smallest molecules can pass through the holes or pores in the membrane, namely water molecules, mineral salt molecules, and molecules of small to medium molecular weight.

More precisely, said membrane 3 is designed in such a manner that, when the difference between the pressure that is exerted on at least a portion of the membrane on the same side as the blood compartment 12 and the pressure that is exerted on said portion of the membrane on the same side as the dialysate compartment 14 is greater than a given threshold value, said portion of the membrane allows an aqueous fraction of the blood to pass into the dialysate compartment 14 in a convective phenomenon known as "ultrafiltration" (UF). Conversely, said membrane 3 is designed in such a manner that, when the difference between the pressure that is exerted on said portion of the membrane 3 on the same side as the dialysate compartment 14 and the pressure that is exerted on said portion of the membrane on the same side as the blood compartment 12 is greater than a given threshold value, said portion of the membrane allows the dialysate to pass into the blood compartment 12 in a phenomenon known as "back-filtration" or "retrofiltration" (RF).

The difference between the mean pressure in the blood compartment and the mean pressure in the dialysate compartment is referred to as the mean transmembrane pressure. Said mean is taken over the surface area of the membrane.

The dialysis membrane may be made in the form of capillary fibers, the blood flowing along the insides of the fibers, and the dialysate flowing along the outsides of said fibers.

Said blood compartment 12 has a blood inlet 201 designed to be connected via an arterial line L1 to a fistula in the patient so as to extract the blood from the body of the patient to be treated, and a blood outlet 202 designed to be connected via a venous line L2 to a vein of the patient so as to feed the blood back into body of the patient after treatment. The term "line" means a tube optionally provided with a plurality of branches or portions and through which a liquid can flow.

Figure 5:
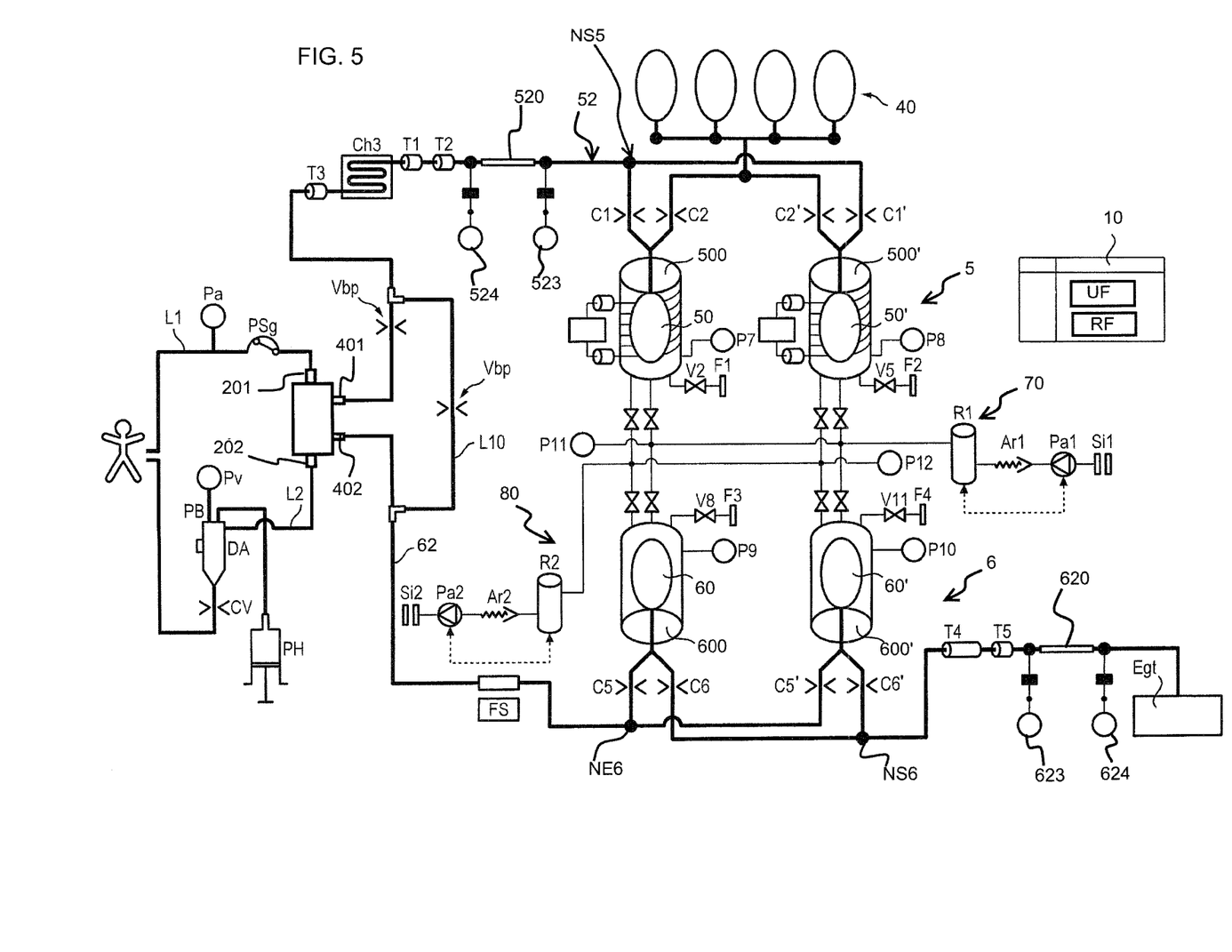
FIG. 5 is a diagram of the machine of the invention, that, in addition to what is shown in FIG. 1, shows, in particular the two ventricle bags and the two discharge bags.

In the example shown in FIG. 5, the arterial line L1 is also provided with a blood pump Psg, and with a pressure sensor Pa, also referred to as an "arterial pressure sensor". The venous line L2 is provided with a pressure sensor Pv, also referred to as a "venous pressure sensor", a bubble trap PB, and an air detector DA. Advantageously, the pressure sensor Pv is connected to the bubble trap PB. Preferably, said venous line L2 is also provided with an anticoagulant injection system, such as a heparin pump PH.

The mean pressure in the blood compartment 12 results from the venous return pressure plus the pressure related to the head loss in the blood compartment 12, which head loss depends on the viscosity of the blood and on its flow rate. The venous return pressure depends on the needle and on the vascular access that are used, and on the blood pressure of the patient.

The arterial line L1, the venous line L2 and the blood compartment 12 form the blood circuit of the machine.

Said dialysate compartment 14 has a dialysate inlet 401 and a dialysate outlet 402. The machine also includes a dialysate feed system 5 that includes a dialysate feed line 52 connected to the inlet 401 of the dialysate compartment 14, and a dialysate discharge system 6 that includes a discharge line 62 connected to the outlet 402 of the dialysate compartment 14. Said dialysate feed system 5, the dialysate compartment 14, and said dialysate discharge system 6 form the dialysate circuit.

Said machine also includes a control unit 10, such as a programmable controller.

Said control unit is in the form of an electronic and computer system that, for example, includes a microprocessor and a working memory. Said control unit also has a data input interface, for entering data such as "dry" weight of the patient and weight of said patient before the treatment, as described in detail below.

Thus, when it is specified that the control unit includes means for performing a given action, that signifies that the corresponding electronic and computer system includes instructions making it possible to perform said action.

Said control unit includes ultrafiltration control means UF and back-filtration control means RF. As recalled above, ultrafiltration corresponds to an aqueous quantity of the body fluid passing, through at least a portion of the membrane 3, from the blood compartment 12 into the dialysate compartment 14. Conversely, back-filtration or "retrofiltration" corresponds to the dialysate passing, through at least a portion of the membrane 3, from the dialysate compartment 14 into the blood compartment 12. Operation of said ultrafiltration control means UF and of said back-filtration means RF is described in detail below.

Said dialysate feed system 5 also includes at least one flexible bag 50, referred to as a "ventricle bag", designed to contain the dialysate and connected to said feed line 52.

Preferably, as shown in FIG. 5, said dialysate feed system 5 includes an additional ventricle bag 50' that is connected in parallel with the portion of the feed line 52 to which said ventricle bag 50 is connected.

Each ventricle bag 50, 50' is housed in a substantially sealed enclosure 500, 500' that can be put under pressure, and optionally put under suction. Each ventricle bag 50, 50' can thus be put under pressure by pressurizer means 70 and, optionally, be put under suction by a vacuum generator 80.

Said pressurizer means 70 comprise a pressurized gas injector device, such as an air compressor or a compressed gas bottle suitable for injecting the pressurized gas into the sealed enclosure 500, 500' in which the ventricle bag 50, 50' is housed. Said enclosure has an outlet 501 that is suitable for being caused to open by a solenoid valve in order to reduce the pressure in the enclosure. Each enclosure 500, 500' is maintained at a temperature suitable for the sterile dialysate to be substantially at 37° C.

By applying pressure to the ventricle bag 50 or 50' and by regulating the applied pressure, by means of the pressure difference measured across the terminals of the head-loss tube 520 as described in detail below, it is possible to maintain a fixed flow rate of dialysate in the dialysate compartment for a given time in reliable and accurate manner, and thus to keep the back-filtration operations under control as explained below. Applying pressure and regulating the pressure applied to the ventricle bag 50 or 50' also makes it possible, by adjusting the pressure applied to the discharge bag 60 or 60' as described in detail below, to maintain a given mean pressure in the dialysate compartment for a given time, and thus to keep the ultrafiltration operations under control.

The two ventricle bags 50, 50' are suitable for being put under pressure/suction independently from each other.

Said or each ventricle bag 50, 50' is also provided with an inlet for connecting to a dialysate feed source 40. This dialysate feed source is preferably a feeder bag of volume, e.g. 5 liters (L), larger than the volume, e.g. 150 milliliters (mL), of said ventricle bag 50, 50'.

In a variant, the external feed source may be a continuous dialysate production device.

As shown in FIG. 5, each ventricle bag 50, 50' is also provided with a downstream close/open member C1, C1' for closing/opening the feed line that, in the open state, allows dialysate to flow from the corresponding bag 50, 50' to the inlet 401 of the dialysate compartment, under the effect of pressure applied to said ventricle bag by the corresponding means 70, and, in the closed state, prevents said dialysate from flowing. Each downstream close/open member C1, C1' of the feed line is situated between the corresponding bag 50, 50' and the connection outlet node NS5 for connection to the two bags 50, 50'. Each ventricle bag 50, 50' is also provided with an upstream close/open member C2, C2' that makes it possible to allow or not to allow said ventricle bag 50, 50' to be fed by the feed source 40.

Each portion of the dialysate feed line 52 at which an upstream close/open member C2, C2' or downstream close/open member C1, C1' is situated is flexible. Each of said close/open members C2, C2', C1, C1' is formed by a clamp controllable firstly to clamp, from the outside, the wall of said flexible portion of the feed line 52 in such a manner as to close said portion, and secondly to leave said flexible portion of said feed line 52 open.

Use of two ventricle bags 50, 50' connected in parallel and feedable by an external source facilitates manipulations and avoids the need to open the enclosures 500, 500' during the dialysis. During a session, the ventricle bags are left in their enclosures while they are refilled via the feeder bags that are outside the enclosures. The presence of two ventricle bags and of the alternate clamping system formed by the members C1 to C2' makes it possible to fill the ventricle bags in succession and in alternation from the feeder bag(s) containing the reserve. This makes it possible to feed the dialysate feed line continuously from one of the ventricle bags disposed in the enclosure under pressure.

Putting the enclosure of a ventricle bag 50 or 50' under suction by means of the vacuum generator 90 makes it possible, when the upstream close/open member C2 or C2' is in the open state, and when the corresponding downstream close/open member C1 or C1' is in the closed state, to suck out the dialysate contained in the feed source 40 for filling said ventricle bag 50 or 50' (see FIG. 5).

In order to cause the dialysate to flow through the feed line 52, the control unit 10 causes the downstream member C1 or C1' of one of the ventricle bas 50 or 50' to open, and causes the corresponding upstream member C2 or C2' to close. By using two ventricle bags connected in parallel, it is possible to refill one of them while the other is being used.

The dialysate feed line 52 is provided with a flow constriction 520 for generating head loss and for making it possible to regulate the pressure applied to the ventricle bag 50 or 50' as a function of the pressure difference measured across the terminals of said constriction. In particular, said line 52 is provided with means for measuring the pressure difference between the inlet and the outlet of said flow constriction 520. This constriction 520 may be formed at least in part by a calibrated tube of constant cross-section that forms a throat over a predetermined length. Said flow constriction 520 is situated between the bags 50, 50' and the inlet 401 of the dialysate compartment 14.

Said pressurizer means advantageously maintain a pressure on the ventricle bag 50 or 50' that is sufficient to cause the dialysate to flow. The feed line is calibrated so that, for a determined pressure applied to the ventricle bag 50 or 50', the flow rate of dialysate through said line has a value that is substantially constant.

Such a system formed of a head-loss tube and of means for measuring the pressure difference across the terminals of the constriction, makes it possible, in particular, to determine the flow rate of dialysate flowing through said feed line and into the dialysate compartment. By means of the dialysate flow rate measured in this way, the control unit 10 can regulate the pressure applied to the ventricle bag 50 or 50' in order to obtain the desired flow rate of dialysate flowing into the dialysate compartment, and in order to maintain that flow rate accurately and reliably at a given value for a given time.

Figure 1:
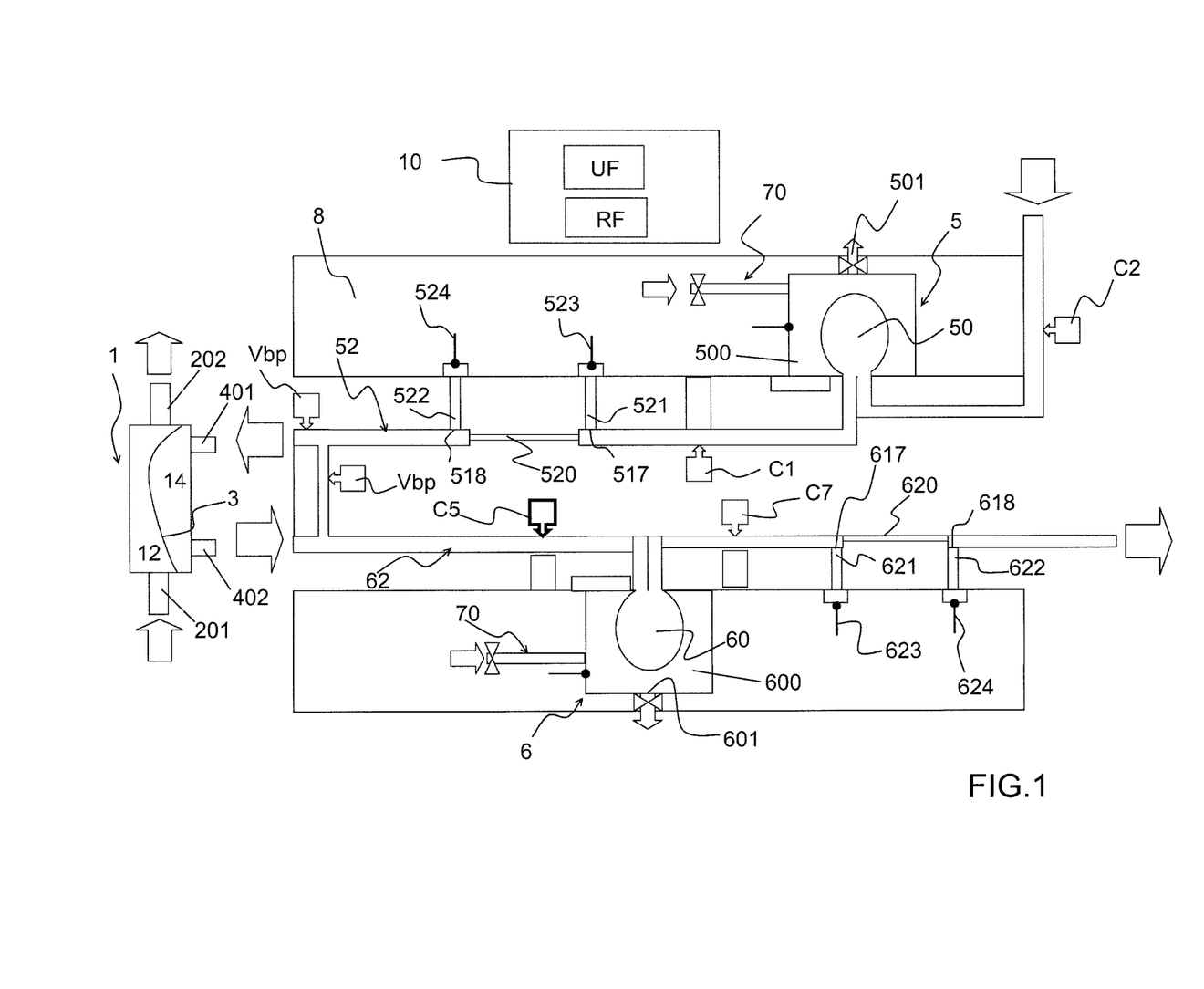
FIG. 1 is a simplified diagram of the dialysis machine of the invention.

As shown more particularly in FIG. 1, said means for measuring the pressure difference across the terminals of the constriction 520 in the feed line 52 comprise two pressure measurement orifices 517, 518 provided, in the peripheral wall of said line 52, one upstream from said constriction 520 and the other downstream therefrom. Each pressure measurement orifice 517, 518 is associated with a pressure sensor 523, 524. Each pressure sensor 523, 524 is arranged relative to the corresponding pressure measurement orifice 517, 518 in such a manner as to measure the pressure in the feed line 52 at said pressure measurement orifice 517, 518 while also being spaced apart from said orifice 517, 518 so as not to be in contact with the dialysate flowing through the line 52, 62.

Advantageously, a duct 521, 522, preferably provided with a filter 17 (see FIG. 2) permeable to air and impermeable to infectious agents and to liquids, is interposed between each pressure sensor 523, 524 and the corresponding pressure measurement orifice 517, 518 that opens out in the feed line.

Figure 2:
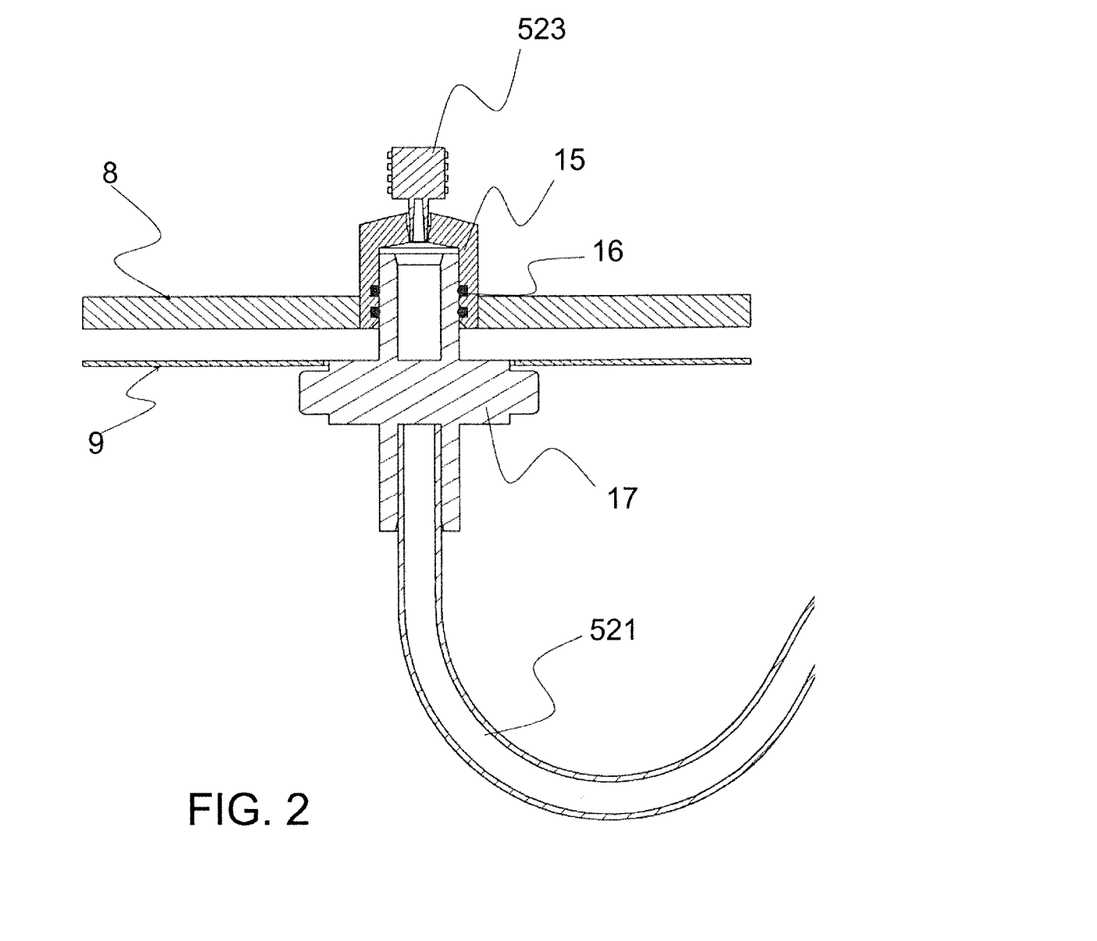
FIG. 2 is a diagrammatic view of a pressure sensor fastened to the frame of the machine and of a pressure measurement duct provided with a filter.

Thus, as shown in FIG. 2, the pressure sensor 523 is mounted in a cavity of the frame 8 of the machine by means of a support piece 15. Said support piece 15 is hollow and is designed to be coupled to the corresponding duct 521. A sealing gasket 16, such as an O-ring seal, provides pneumatic sealing between the support 15 of the pressure sensor and the duct 521. In the state in which a cassette 9 is inserted in the frame, the free end of the duct 521, which end is preferably provided with a filter 17, is engaged in the support piece 15 so that the pressure sensor is capable of measuring the pressure in said duct 521 and thus the pressure in the line 52 at the corresponding pressure measurement orifice. The pressure sensor 524 and the pressure measurement duct 522 associated with the pressure measurement orifice 518 are arranged in the same manner as shown in FIG. 2 for the pressure sensor 523.

It is possible to make provision for the pressure in the arterial line L1 and for the pressure in the venous line L2 to be measured in the same manner as for the pressure measurement across the terminals of the constriction 520. It is thus possible to make provision for the pressure sensor Pa and the pressure sensor Pb to be fastened to a portion of the frame that is spaced apart from a pressure orifice provided in the corresponding line L1, L2. An arrangement corresponding to the arrangement shown in FIG. 2 can then be used to enable the pressure sensors Pa and Pv to measure the pressure in the corresponding line L1, L2 without any risk of contamination.

Said machine includes an open/close system for opening/closing the dialysate discharge line 62. When it is in the open state, said open/close system allows the dialysate present at the outlet of the dialysate compartment 14 to flow through said discharge line and fill one of the discharge bags 60 or 60' as described in detail below, and, when it is in the closed state, said open/close system prevents the dialysate present at the outlet of said dialysate compartment 14 from flowing through said discharge line 62 so that, when the pressure in the dialysate compartment is sufficient, said dialysate passes through the membrane 3 into the blood compartment. This open/close system is described in detail below.

Said dialysate discharge system 6 includes at least one discharge bag 60 that is preferably flexible and that has an inlet and an outlet connected to the dialysate discharge line 62. Said open/close system includes an upstream open/close member C5 situated between the outlet 402 of the dialysate compartment 14 and said discharge bag 60.

Said dialysate discharge system 6 includes at least one other discharge bag 60' connected in parallel with said discharge bag 60. Thus, the discharge bag 60 and the discharge bag 60' are situated on respective ones of two branches of the discharge line 62. In other words, starting from the outlet of the dialysate compartment 14, the discharge line 62 divides, upstream from the discharge bags 60, 60' into two parallel branches, one of which is provided with the discharge bag 60 and the other of which is provided with the discharge bag 60'. These two branches are connected to each other downstream from the bags 60, 60' and upstream from the flow-section constriction 620 as described in detail below.

Said open/close system includes another upstream open/close member C5' situated between said other discharge bag 60' and the connection inlet node NE6 for connection to the discharge bags 60, 60'.

In a manner similar to with the upstream members C5, C5', each discharge bag 60, 60' is provided with a downstream close/open member C6, C6' situated between the corresponding discharge bag 60, 60' and the connection outlet node NS6 for connection to the discharge bags 60, 60'.

Each portion of the dialysate discharge line 62 where an upstream close/open member C5, C5' or downstream close/open member C6, C6' is situated is flexible. Each of said upstream or downstream close/open members C5, C5', C6, C6' for opening or closing the dialysate discharge line 62 is formed by a clamp controllable firstly to clamp, from the outside, the wall of said flexible portion of the discharge line 62 in such a manner as to close said portion, and secondly to leave said flexible portion of said discharge line 62 open.

Such a set of upstream close/open members C5, C5' and of downstream close/open members C6, C6' associated with discharge bags 60, 60' makes it possible, when the upstream member C5, or respectively C5', is in the open state, and when the downstream member C6, or respectively C6', is in the closed state, to fill the discharge bag 60, or respectively 60', and, when the upstream member C5, or respectively C5', is in the closed state, and when the downstream member C6, or respectively C6', is in the open state, to empty said discharge bag 60, or respectively 60'.

When the discharge system 6 is formed by one or more discharge bags 60, 60', it is considered that the discharge line 62 is open when the dialysate can flow through said line to fill said bag or one of said bags.

The means for discharging the dialysate and the liquid present in the discharge bag 60 or 60' may be formed by gravity if the configuration of the discharge bag lends itself to such means, and/or by pressurizer means 70, preferably common to the means that serve to put the ventricle bags 50, 50' under pressure. When such common pressurizer means are provided, said or each bag 60, 60' is housed in a substantially sealed enclosure 600, 600' suitable for being put under pressure by said pressurizer means 70. Said enclosure has an outlet 601 that is suitable for being caused to open by a solenoid valve in order to reduce the pressure in the enclosure.

It is also possible to make provision for each enclosure 600, 600' that houses a discharge bag 60, 60' to be connected to a vacuum generator 80. The vacuum generator 80 and/or the pressurizer means 70 make it possible to apply pressure or suction to the discharge bag 60 or 60', in such a manner as to adjust the mean pressure in the dialysate compartment 14 during an ultrafiltration stage. The downstream member C6 or C6' of the discharge bag 60 or 60' that is then used to adjust the mean pressure in the dialysate compartment 14, is closed while the corresponding upstream member C5 or C5' is open.

Said vacuum generator 80 may be a common vacuum generator 80 for putting the enclosures of the dialysate feed system 5 and the enclosures of the discharge system 6 under suction.

Said machine comprises means for determining the quantity of dialysate and of liquid recovered in the discharge bag 60 or 60' as it empties.

Said means for determining the quantity of dialysate and liquid recovered in the discharge bag(s) 60, 60' comprise a flow constriction 620, provided in the dialysate discharge line 62 and situated downstream from said discharge bags 60, 60', and measurement means for measuring the pressure difference across the terminals of said flow constriction 620.

Said means for measuring the pressure difference across the terminals of the constriction 620 of the discharge line 62 are similar to those associated with the constriction 520 of the feed line 52.

Thus, said means for measuring the pressure difference across the terminals of the constriction 620 in the discharge line 62 comprise two pressure measurement orifices 617, 618 provided, in the peripheral wall of said line 62, one upstream from said constriction 620 and the other downstream therefrom.

Each pressure orifice 617, 618 is associated with a pressure sensor 623, 624 arranged in such a manner as to measure the pressure in the line 62 at said orifice 617, 618 while also being spaced apart from said orifice 617, 618 so as not to be in contact with the dialysate flowing through the line 62.

In a manner similar to the measurement means for measuring the pressure difference across the terminals of the constriction 520, a filter that is permeable to air and impermeable to infectious agents and to liquids, is interposed between each pressure sensor 623, 624 and the corresponding pressure measurement orifice 617, 618. In particular, each pressure sensor 623, 624 is mounted in a cavity of the frame 8 of the machine by means of a hollow support piece that is designed to be coupled to the duct 621, 622 connected to the corresponding pressure measurement orifice 617, 618.

In a manner similar to the arrangement shown in FIG. 2 for the sensor 523, a sealing gasket, such as an O-ring seal, provides pneumatic sealing between the support piece, and thus between the pressure sensor 623, 624, and the duct 621, 622. In the state in which a cassette 9 is inserted in the frame, the free end of the duct 621, which end is preferably provided with a filter, is engaged in the support piece so that the pressure sensor is capable of measuring the pressure in said duct and thus the pressure in the line 62 at the corresponding pressure measurement orifice.

The pressure sensors 623, 624 associated with said constriction 620 make it possible to determine the pressure difference across the terminals of the constriction 620 and thus the flow-rate of dialysate and of liquid discharged from the discharge bag 60 or 60', thereby making it possible to determine, by measuring the corresponding flow time, the quantity of dialysate and of liquid recovered in said discharge bag 60 or 60'.

As explained above, said machine has a frame 8 and a cassette 9 that is removable from the frame and that is designed to be inserted in a recess in said frame. Said cassette 9 includes the dialysate lines 52, 62 and the bags 50, 50', 60, 60'.

Said pressure sensors 523, 524, 623, 624 are fastened to the frame 8 of the machine. In the state in which the cassette 9 is inserted in the frame 8 of the machine, the pressure measurement ducts are in pneumatic communication with the pressure sensors. The term "in pneumatic communication" means that the sensor and the corresponding pressure measurement duct are arranged relative to each other in such a manner that the sensor is capable of measuring the pressure prevailing in said duct, and thus the pressure prevailing in the line at the corresponding pressure measurement orifice.

The dialysate feed line 52 and the dialysate discharge line 62 are suitable for being removed from the remainder of the machine, while the corresponding pressure sensors 523, 524, 623, 624 remain fastened to the frame of the machine.

Figures 3, 4:
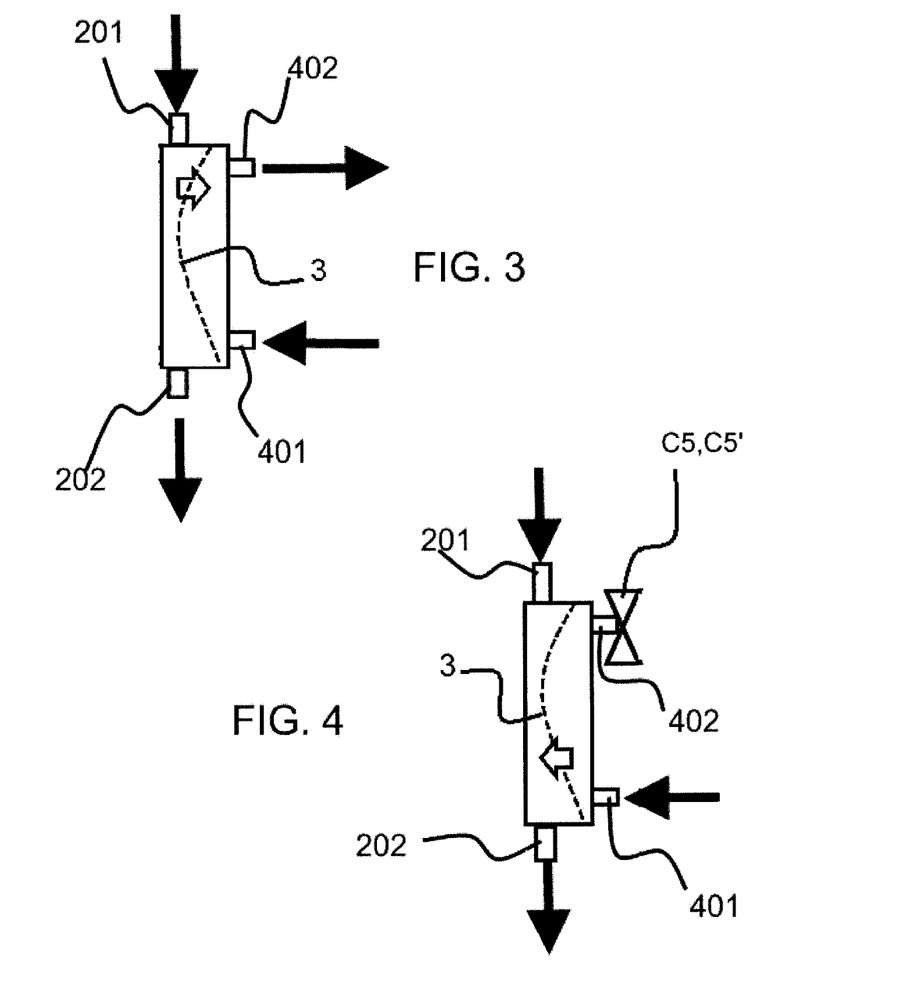
FIGS. 3 and 4 are diagrammatic views respectively showing an ultrafiltration step and a back-filtration step.

As shown in FIG. 4, in order to perform a back-filtration step, said back-filtration control means RF are configured to control said open/close system C5, C5' in such a manner as to close the discharge line 62, and, when said discharge line 62 is closed, in such a manner as to control the pressure applied to the ventricle bag 50 or 50' for back-filtering a given quantity of dialysate.

In particular, in order to cause the dialysate discharge line 62 to be closed with a view to performing a back-filtration step, said back-filtration control means RF are configured to cause each of said upstream open/close members C5, C5' to be closed. In parallel with this back-filtration step, the previously filled discharge bag can be emptied by opening the corresponding downstream member C6 or C6'.

In order to cause the dialysate discharge line 62 to be opened with a view to performing an ultrafiltration step, said ultrafiltration control means UF are configured to cause one of said upstream open/close members, e.g. member C5, to open, and to cause the other upstream open/close member, e.g. the member C5', to close, so that the dialysate at the outlet of the compartment 14 is recovered by one of the two discharge bags, e.g. bag 60.

Advantageously, in parallel, the control unit 10 causes the downstream close/open member C6 associated with the discharge bag 60 of which the upstream member C5 is open to close, so as to enable said discharge bag 60 to fill.

The control unit also causes the downstream close/open member C6' associated with the discharge bag 60' of which the upstream member C5' is closed to open, so as to enable said discharge bag 60' to empty and so as to measure the quantity recovered in said bag.

Even if one of the branches of the line 62 is closed, the dialysate that exits from the dialysate compartment 14 can flow through said line 62 via the other branch and can fill the corresponding discharge bag, so that said line 62 is considered to be open.

Said ultrafiltration control means UF are also configured so that, in the next ultrafiltration step, the other upstream open/close member C5' associated with the discharge bag 60' is caused to open, and said upstream open/close member C5 associated with the discharge bag 60 is caused to close. In parallel, the control unit causes the downstream close/open member C6' associated with the discharge bag 60 of which the upstream member C5' is open to close. In parallel, the control unit 10 causes the downstream close/open member C6 associated with the discharge bag 60 of which the upstream member C5 is closed to open, so as to empty said bag and so as to measure the quantity recovered in said bag.

A discharge bag can be emptied during a back-filtration step and/or during an ultrafiltration step so that no time needs to be dedicated specifically to the emptying operation. Measuring the quantity of dialysate and of liquid recovered in the discharge bag 60 or 60' makes it possible to adjust the quantity of dialysate to be back-filtered for the next back-filtration step and/or to adjust the aqueous quantity to be ultrafiltered for the next ultrafiltration step.

Ultrafiltration makes it possible to extract an aqueous fraction from the blood as shown in FIG. 3. In particular, in a patient whose kidneys are no longer functioning, urine ceases to be produced, and the water from what the patient eats and drinks is no longer removed to a sufficient extent. This then results in the patient being overweight, which can be dangerous to the patient's health. In order to remove the excess water from the blood, it is then possible to subject the blood to ultrafiltration.

In order to increase the effectiveness of the treatment performed on the blood, the machine is also designed to make it possible to remove from the blood a fraction of liquid that is greater than the fraction that corresponds to the excess water in the blood. In which case, that major extraction must be compensated for by reinjecting dialysate into the blood so as to compensate for the volume of liquid extracted in addition to the volume of liquid that corresponds to the excess water in the blood. These ultra-filtration and back-filtration steps make it possible to improve the purification of the patient's blood while also preserving the patient's water balance.

Thus, at the start of a dialysis session, and on the basis of the real and "dry" weights data that is input, the control unit 10 determines the quantity of the excess aqueous fraction to be removed from the body fluid, which quantity is referred to as the "excess aqueous quantity". The "dry" weight of the patient is the weight of the patient when said patient does not have any excess water in the blood.

The control unit 10 then controls the ultrafiltration and back-filtration steps so as to extract through the dialysis membrane 3 an aqueous quantity of the body fluid, which quantity is referred to as the "gross aqueous quantity to be removed" and is greater than said excess aqueous quantity that is defined, and so as to back-filter a quantity of dialysate that is substantially equal to the difference between said gross aqueous quantity to be removed and said excess aqueous quantity. The difference between said gross aqueous quantity to be removed and said excess aqueous quantity is also referred to as the "net ultrafiltered quantity".

A treatment session comprises a plurality of ultrafiltration steps in alternation with back-filtration steps. The number of alternations is preferably not less than 1000.

The succession of an ultrafiltration step and of a back-filtration step is defined as forming a cycle. Thus, during a treatment session, said control unit thus performs a given number N of cycles. In particular, each cycle, referenced by the index $i$, where $i$ lies in the range 1 to N, is made up of an ultrafiltration step of duration $Te\_uf\_i$ and of a back-filtration step of duration $Te\_rf\_i$. As recalled above, the index "$i$" corresponds to the cycle $i$ in question.

As explained above, said control unit 10 determines the excess aqueous quantity in the body fluid, referenced $Q\_aq\_excess$ that is to be removed. Then, for each cycle $i$, said control unit defines the durations $Te\_uf\_i$ and $Te\_rf\_i$, controls the members C5, C5', and, where applicable, C6, C6', accordingly, and controls the pressurizer means 70, and, where applicable, the vacuum generator 80, in such a manner that:

$Q\_aq\_excess$=Sum over $i$, where $i$ lies in the range 1 to N, of $$K \times [(Pa\_i + Pv\_i)/2 - P14\_uf\_i] \times Te\_uf\_i - (Dd\_rf\_i \times Te\_rf\_i)$$

where:

K is a predefined coefficient of ultrafiltration that is specific to the membrane and that expresses the ultrafiltration capacity thereof;

Pa_i is the pressure upstream from the blood compartment 12 during the ultrafiltration step of the cycle $\underline{i}$;

Pv_i is the pressure downstream from the blood compartment 12 during the ultrafiltration step of the cycle $\underline{i}$;

P14_uf_i is the mean pressure in the dialysate compartment 14 during the ultrafiltration step of the cycle $\underline{i}$; and Dd_rf_i is the flow rate of dialysate in the dialysate compartment 14 during the back-filtration step of the cycle $\underline{i}$, said flow rate Dd_rf_i being a function of the pressure applied to the ventricle bag 50 or 50'.

For a quantity Q_aq_excess expressed in milliliters (mL), the pressures expressed in millimeters of mercury (mmHg), the time expressed in hours (h), and the flow rate expressed in milliliters per hour (mL/h), said coefficient K of the dialysis membrane is expressed in mL/(h×mmHg). Said coefficient K of a dialysis membrane generally lies in the range 50 mL/h×mmHg) to 90 mL/(h×mmHg).

The operations performed by the control unit and in particular by the ultrafiltration control means UF and by the back-filtration control means RF are described in detail below.

After determining the excess aqueous quantity present in the blood, referenced Q_aq_excess, the control unit determines an aqueous quantity to be removed from the blood, referenced Q_aq_gross, and greater than Q_aq_excess. The extra aqueous quantity removed from the blood relative to the excess aqueous quantity in the blood Q_aq_excess is arranged to be compensated for by back-filtration of a corresponding quantity of dialysate. The control unit then determines the quantity of aqueous fraction to be removed from the body fluid at each cycle i, referenced Q_aq_gross_i, so that Q_aq_gross=Sum over of Q_aq_gross_i.

The head loss in the feed line is such that, during an ultrafiltration step, the aqueous fraction of the blood passes more easily through the membrane under the effect of the transmembrane pressure than the dialysate passes from the ventricle bag 50 or 50' towards the dialyzer 1.

In order to perform the ultrafiltration step of a cycle $\underline{i}$, said ultrafiltration control means UF control said open/close system C5, C5' of the dialysate discharge line 62 so as to open said dialysate discharge line 62 for the duration Te_uf_i, and, when the dialysate discharge line 62 is open, control the pressure, referenced P5_uf_i, applied to the ventricle bag 50 or 50' and the pressure, or suction, to be applied to the discharge bag 60 or 60', so as to remove the aqueous quantity Q_aq_gross_i from the blood.

To this end, said ultrafiltration means determine the mean pressure P14_uf_i to be reached in the dialysate compartment 14 and the corresponding duration Te_uf_i that satisfies the relationship:

$$Q\_aq\_gross\_i = K \times (P14\_uf\_i - P12\_uf\_i) \times Te\_uf\_i$$

K being, as explained above, a predefined coefficient that is specific to the membrane and that expresses the ultrafiltration capacity thereof;

with P12_uf_I=(Pa_i+Pv_i)/2, i.e. the mean pressure in the blood compartment 12;

where Pa_i is the pressure upstream from the blood compartment 12 during the ultrafiltration step of the cycle $\underline{i}$; and where Pv_i is the pressure downstream from the blood compartment 12 during the ultrafiltration step of the cycle $\underline{i}$.

For said duration Te_uf_i, said ultrafiltration control means UF control the pressure P5_uf_i to be applied to said ventricle bag 50 or 50' and the pressure, or suction, to be applied to be the discharge bag 60 or 60', making it possible to obtain said pressure P14_uf_i in the dialysate compartment 14.

Advantageously, said pressure P5_uf_i is regulated by means of the pressure sensors 523, 524 associated with the constriction 520 so as to obtain a fixed flow rate of dialysate regardless of the mean pressure in the dialysate compartment.

In order to cause the back-filtration step of a cycle $\underline{i}$ to take place, said back-filtration control means RF control said open/close system C5, C5' of the dialysate discharge line 62 so as to close said dialysate discharge line 62 for the duration Te_rf_i. Then, for said duration Te_rf_i, said back-filtration control means RF control the pressure, referenced P5_rf_i, applied to said ventricle bag 50 or 50' so as to back-filter a given quantity of dialysate Q_rf_i.

Preferably, said quantity of dialysate to be back-filtered Q_rf_i is defined as being equal to the quantity of dialysate and of liquid that was recovered in the discharge bag 60 or 60' during a preceding ultrafiltration step, less the quantity of dialysate that flowed from the ventricle bag 50 or 50' during said preceding ultrafiltration step.

Said back-filtered quantity of dialysate Q_rf_i is equal to Dd_rf_i×Te_rf_i, where Dd_rf_i is the flow rate of dialysate in the feed line 52 that enters the dialysate compartment 14. Said back-filtration control means RF then control the pressure P5_rf_i applied to the ventricle bag 50 or 50' in such a manner as to obtain the desired flow rate of dialysate Dd_rf_i. The real flow rate of dialysate Dd_rf_i that passes through the feed line 52 is computed by means of the pressure difference measured across the terminals of the constriction 520, and the control unit regulates the pressure P5_ref_i so as to maintain the flow rate of dialysate Dd_rf_i at the desired value.

Figure 6:
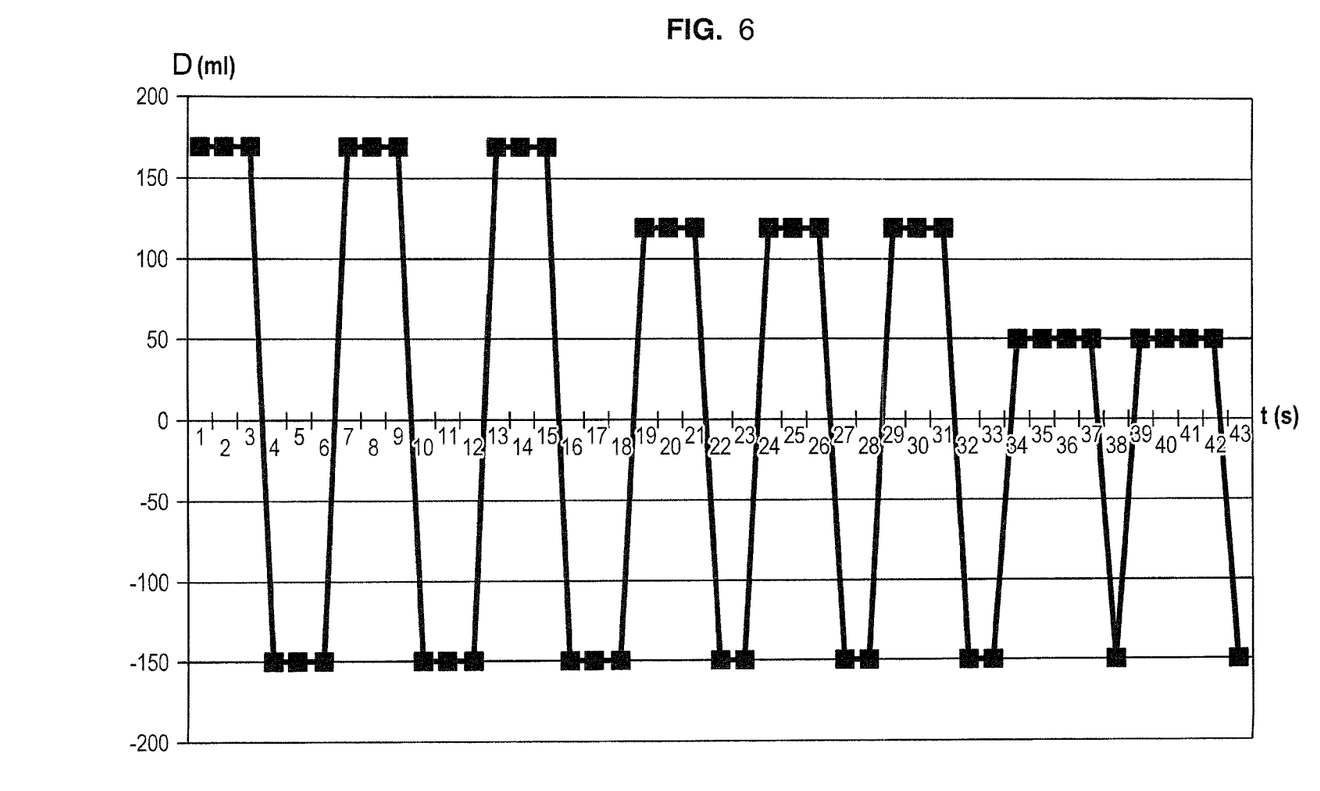
FIG. 6 is a graph showing, as a function of time, the transmembrane flow rate that results from a plurality of ultrafiltration and back-filtration cycles.
Figure 7:
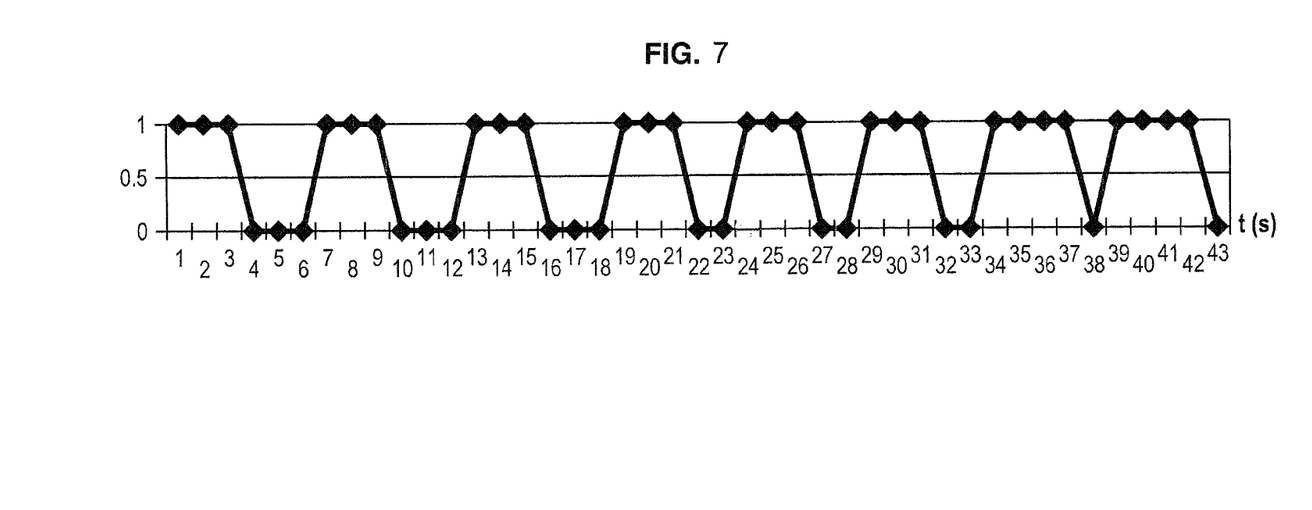
FIG. 7 is a graph showing the open configuration (1) or the closed configuration (0) of the discharge line for the plurality of ultrafiltration and back-filtration cycles of FIG. 6.

An example of treatment is shown in FIGS. 6 and 7 for a duration of 43 seconds (s).

FIG. 6 shows, as a function of time t(s), the transmembrane flow rate D (mL) that results from a plurality of ultrafiltration and back-filtration cycles. In this example, during a first ultrafiltration step of 3 seconds, the ultrafiltration flow rate is equal to 170 milliliters per minute (mL/min). This ultrafiltration is followed by a back-filtration step, also of 3 seconds, resulting in a negative flow rate of 150 mL/min. These two steps form a cycle that is repeated twice. The fourth cycle, also repeated twice, comprises an ultrafiltration step of the same duration, but of lower flow rate relative to the three preceding cycles. The corresponding back-filtration steps have the same flow rate but are of shorter duration relative to the three preceding cycles. Finally, the seventh cycle, which is repeated once, comprises an ultrafiltration step of duration longer than the duration of the other cycles but of lower flow rate, while the corresponding back-filtration step is still performed with the same flow rate but over a shorter duration than the duration of the other cycles. It is thus possible, for each ultrafiltration step and back-filtration step, to adjust the corresponding flow rate and duration of the step. FIG. 7 shows the open configuration (1) or the closed configuration (0) of the discharge line for the plurality of ultrafiltration and back-filtration cycles of FIG. 6.

It should be noted that each of these three groups of cycles makes it possible to obtain the same net (or overall) ultrafiltered quantity from different back-filtered quantities by adjusting the pressure applied to the discharge bag 60 or 60' during the ultrafiltration operations and/or by adjusting their durations.

The dialysis machine of the invention is also provided with conventional components for reliably and effectively treating the body fluid to be treated, in particular a blood leak detector FS provided in the discharge line 62. Advantageously, the control unit is configured to make it possible to calibrate the flow meters relative to each other.

In order to make the figures clearer, the connections between the control unit 10 and the various components of the machine with which said control unit 10 communicates for controlling them and/or for retrieving data, are not shown. In particular, such components are the members C1 to C6', CV, the solenoid valves, the pressure sensors, the temperature sensors, as well as the pressurizer means 70, the vacuum generator 80, the blood pump Psg and the injection system PH, and the air detector DA or the blood leak detector FS.

Each enclosure 500, 500' is provided with heater or preheater means for heating or preheating the enclosure. Each enclosure 500, 500', 600, 600' is also provided with an air vent valve V2, V5, V8, V11 associated with an air filter F1, F2, F3, F4, and with a pressure sensor P7, P8, P9 and P10.

The pressurizer means 70 comprise the following elements: a compressed air reservoir R1, a pressure sensor P11 of the reservoir R1, a compressor Pa1, a compressed air check valve Ar1, and a compressed air filter and silencer Si1.

The vacuum generator 80 comprises an air vacuum reservoir R2, a pressure sensor P12 of the reservoir R2, a vacuum pump Pa2, an air vacuum check valve Art, and an air vacuum air filter and silencer Si 2.

The feed line 52 is also provided with heater means Ch3 for heating the dialysate that are associated with temperature measurement means T1, T2, T3. The feed line 62 is also provided with temperature measurement means T4, T5 downstream from the bags 60, 60'.

Advantageously, the venous line L2 is also provided with a close/open member CV, such as a clamp.

The present invention is in no way limited to the embodiments described and shown, and the person skilled in the art can make any variant to them that lies within the spirit of the invention.

Such a solution makes it possible to omit specific draw-off and reinjection lines such as they exist in solutions known from the state of the art.

In addition, the machine of the invention requires only one dialyzer filter for each session. It is not necessary to provide two filters in series as such filters exist in solutions known from the state of the art.

The machine includes at least one by-pass line L10, and one or more associated close/open members Vbp. The by-pass line L10 is used to prime and calibrate the dialysate circuit, and to make it possible to avoid injecting into the dialyzer dialysate that is defective, e.g. due to a temperature problem.

Advantageously, the discharge line of the dialyzer is connected to a recovery receptacle or to a drain system Egt.

The invention claimed is:

1. A dialysis machine making it possible to treat a body fluid, said machine comprising: a dialyzer including an enclosure housing a dialysis membrane that subdivides the enclosure into a body fluid compartment for passing said body fluid, and a dialysate compartment for passing dialysate; said body fluid compartment having a body fluid inlet and a body fluid outlet, and said dialysate compartment having a dialysate inlet and a dialysate outlet; a dialysate feed system comprising a dialysate feed line connected to the inlet of the dialysate compartment; and a dialysate discharge system comprising a dialysate discharge line connected to the outlet of the dialysate compartment; a control unit that comprises: ultrafiltration control means that sends an aqueous quantity of the body fluid to pass through a portion of the membrane from the body fluid compartment into the dialysate compartment; and back-filtration control means configured to make the dialysate pass through at least a portion of the membrane, from the dialysate compartment into the body fluid compartment; wherein the dialysate feed line is provided with a flow constriction, and said machine further comprises means for measuring the pressure difference across the terminals of said flow constriction; in that said dialysate feed system further comprises: at least one ventricle flexible bag designed to contain the dialysate and connected to said feed line upstream from said flow constriction, said ventricle bag being contained in an enclosure; and pressurizer means for putting the ventricle bag under pressure by pressurizing said enclosure; and in that said machine further comprises an open/close system for opening/closing the dialysate discharge line, which system, when in the open state, allows the dialysate present at the outlet of the dialysate compartment to flow through said discharge line, and, when in the closed state, prevents the dialysate present at the outlet of said dialysate compartment from flowing through said discharge line said back-filtration control means being configured to: control said open/close system so as to close the discharge line; and when said discharge line is in the closed state, control the pressure applied to said ventricle bag as a function of the pressure difference measured across the terminals of the constriction, so as to obtain a given flow rate of dialysate.

2. A machine according to claim 1, said dialysate discharge system further comprises at least one discharge bag that has an inlet and an outlet that are connected to the dialysate discharge line; and in that said open/close system comprises an upstream open/close member situated between the outlet of the dialysate compartment and said discharge bag; and in that said machine further comprises means for determining the quantity of dialysate and of liquid recovered in said discharge bag.

3. A machine according to claim 2, wherein said dialysate discharge system further comprises at least one other discharge bag connected in parallel with said discharge bag; and in that said open/close system further comprises another upstream open/close member situated between said other discharge bag and the connection inlet node for connection to the discharge bags; and in that said machine further comprises means for determining the quantity of dialysate and of liquid recovered in said other discharge bag.

4. A machine according to claim 3, wherein said means for determining the quantity of dialysate and of liquid recovered in the discharge bag(s) comprise a flow constriction provided in the dialysate discharge line and situated downstream from said discharge bag(s), and measurement means for measuring the pressure difference across the terminals of said flow constriction.

5. A machine according to claim 4, wherein, in order to cause the dialysate discharge line to be closed with a view to performing a back-filtration step, said back-filtration control means are configured to cause each of said upstream open/close members associated with the discharge bags to close; and in that, in order to cause the dialysate discharge line to be opened with a view to performing an ultrafiltration step, said ultrafiltration control means are configured to cause one of said upstream open/close members to open, and to cause the other upstream open/close member to close.

6. A machine according to claim 5, wherein said ultrafiltration control means is configured to act, in the next ultrafiltration step, to cause the other of said upstream open/close members to open and to cause said upstream open/close member to close.

7. A machine according to claim 4, wherein each of the upstream close/open members, and, optionally, each of the downstream close/open members, for closing/opening the discharge line comprises at least one clamp suitable firstly for clamping, from the outside, the wall of a flexible portion of said discharge line in such a manner as to close said portion, and secondly for leaving said flexible portion of said discharge line open.

8. A machine according to claim 3, wherein the or each discharge bag is provided with a downstream open/close member situated downstream from said discharge bag; and in that, after an ultrafiltration step, said control unit is configured to act to cause the downstream open/close member of the previously filled discharge bag to open in order to discharge its contents; and, preferably, in order to determine the quantity recovered in said discharge bag, the control unit is configured to measure the flow rate that flows from said discharge bag, using said means for measuring the pressure difference across the terminals of the constriction situated downstream from said discharge bag.

9. A machine according to claim 8, wherein said control unit acts in parallel with a back-filtration step, to cause the downstream open/close member of the previously filled discharge bag to open in order to discharge its contents; and, preferably, in order to determine the quantity recovered in said discharge bag.

10. A machine according to claim 2, wherein said means for determining the quantity of dialysate and of liquid recovered in the discharge bag or bags comprise a flow constriction provided in the dialysate discharge line and situated downstream from said discharge bag(s), and measurement means for measuring the pressure difference across the terminals of said flow constriction.

11. A machine according to claim 1, wherein said means for measuring the pressure difference across the terminals of the constriction in the feed line, or, respectively across the terminals of the constriction in the discharge line when said constriction is present, comprise: two pressure measurement orifices, one of which is provided upstream from said constriction and the other which is provided downstream from said constriction; and for each pressure measurement orifice, a pressure sensor arranged in such a manner as to measure the pressure in the corresponding line at said orifice, while also being spaced apart from said orifice so as not to be in contact with the dialysate flowing through the line.

12. A machine according to claim 11, wherein a filter that is permeable to air and impermeable to infectious agents and to liquids is interposed between each pressure sensor and the corresponding pressure measurement orifice.

13. A machine according to claim 11, wherein said machine has a frame, and said pressure sensors are fastened to the frame of the machine; and in that the dialysate feed line and the dialysate discharge line are removed from the remainder of the machine, while the corresponding pressure sensors remain fastened to the frame of the machine.

14. A machine according to claim 12, wherein said machine has a frame, and said pressure sensors are fastened to the frame of the machine; and in that the dialysate feed line and the dialysate discharge line are removable from the remainder of the machine, while the corresponding pressure sensors remain fastened to the frame of the machine.

15. A machine according to claim 1, wherein said control unit further comprises means for determining an excess aqueous quantity to be removed from the body fluid; and in that the ultrafiltration control means are configured to extract through the dialysis membrane a gross aqueous quantity of the body fluid to be removed and is greater than said excess aqueous quantity that is defined; the back-filtration control means being configured to back-filter a quantity of dialysate that is substantially equal to the difference between said gross aqueous quantity to be removed and said excess aqueous quantity.

16. A machine according to claim 1, wherein said control unit is configured to act during a treatment session to cause ultrafiltration steps to take place in alternation with back-filtration steps, the number of alternations that is not less than 1000.

17. A machine according to claim 16, for a defined number N of cycles, each cycle i, where i lies in the range 1 to N, is made up of an ultrafiltration step of duration Te_uf_i and of a back-filtration step of duration Te_rf_i;
said control unit is configured to:
determine the excess aqueous quantity in the body fluid, referenced Q_aq_excess that is to be removed;
for each cycle i, define the durations Te_of_i and Te_rf_i, and control the pressurizer means in such a manner that:
Q_aq_excess=Sum over i, where i lies in the range 1 to N, of $K \times [(Pa\_i+Pv\_i)/2-P14\_uf\_i] \times Te\_uf\_i-(Dd\_rf\_i \times Te\_rf\_i)$ where: \

K is a predefined coefficient of ultrafiltration that is specific to the membrane and that expresses the ultrafiltration capacity thereof;
Pa_i is the pressure upstream from the body fluid compartment during the ultrafiltration step of the cycle i;
Pv_i is the pressure downstream from the body fluid compartment during the ultrafiltration step of the cycle i;
P14_of_i is the mean pressure in the dialysate compartment during the ultrafiltration step of the cycle i; and
Dd_rf_i is the flow rate of dialysate in the dialysate compartment during the back-filtration step of the cycle i.

18. A machine according to claim 1, wherein said open/close system for opening/closing the discharge line comprises at least one clamp firstly for clamping, from the outside, the wall of a flexible portion of said discharge line in such a manner as to close said portion, and secondly for leaving said flexible portion of said discharge line open.

19. A machine according to claim 1, wherein the dialysate feed system further comprises an additional ventricle bag, the two ventricle bags for being put under pressure separately by said pressurizer means.

20. A machine according to claim 1, wherein said or each ventricle bag is also provided with an inlet for connection to a dialysate feed source that is of larger volume than the or each ventricle bag.

* * * * *

UNITED STATES PATENT AND TRADEMARK OFFICE
CERTIFICATE OF CORRECTION

PATENT NO.        : 9,717,837 B2
APPLICATION NO.   : 14/349078
DATED             : August 1, 2017
INVENTOR(S)       : Eric Vincent It is certified that error appears in the above-identified patent and that said Letters Patent is hereby corrected as shown below:

In the Claims

Column 24, Claim 17, Line 29: The formula "Te_of_i" after the words "define the durations" should read as "Te_uf_i."

Column 24, Claim 17, Line 44: The formula "P14_of_i" after the words "step of the cycle i;" should read as "P14_uf_i"

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*